US00PP33473P2

(12) United States Plant Patent
Goffreda et al.

(10) Patent No.: US PP33,473 P2
(45) Date of Patent: Sep. 14, 2021

(54) PEACH TREE NAMED 'NJ360'

(50) Latin Name: ***Prunus persica* L.**
Varietal Denomination: NJ360

(71) Applicant: RUTGERS, THE STATE UNIVERSITY OF NEW JERSEY, New Brunswick, NJ (US)

(72) Inventors: Joseph C. Goffreda, Columbus, NJ (US); Anna M. Voordeckers, East Windsor, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/091,077

(22) Filed: Nov. 6, 2020

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./197
See application file for complete search history.

*Primary Examiner* — Annette H Para
(74) *Attorney, Agent, or Firm* — Patrick J. Daugherty; Daugherty & Del Zoppo, Co., LPA

(57) ABSTRACT

A new and distinct peach variety of *Prunus persica* named 'NJ360' is provided. This variety is distinguished from other peach varieties by its unique combination of showy flowers, medium to large, round, semi-freestone fruit, with a red to greyed-purple blush over a bright yellow-white ground, ripening in mid-season, and possessing aromatic, sweet, sub-acid flavor.

6 Drawing Sheets

STATEMENT REGARDING FEDERALLY SPONSORED RESEARCH OR DEVELOPMENT

This invention was made with government support under, contract or grant Multistate Research Project NE-9, entitled Conservation and Utilization of Plant Genetic Resources, awarded or sponsored by the National Institute of Food and Agriculture. The government has certain rights in the invention.

Latin name of genus and species of the plant claimed: *Prunus persica* L.

Variety denomination: 'NJ360'.

BACKGROUND OF THE INVENTION

The present invention relates to a new and distinct variety of peach tree named 'NJ360' that resulted from crossing a peach seedling selection 'H24-128-01224' (non-patented) as the seed parent with 'NJ354' (U.S. Plant Pat. No. 23,669). The new variety differs from seed parent 'H24-128-01224' in that the new variety produces white fleshed fruit that ripen 3 days earlier and have different, more preferable values of flavor and aromatics. The new variety differs from pollen parent 'NJ354' in that the new variety ripens about 2 weeks later and more consistently produces fruit with different, more preferable values of sweetness and flavor. The resulting tree was selected when growing in a cultivated area as the 135$^{th}$ tree in the 14$^{th}$ row of Block H at a fruit research farm in Cream Ridge, N.J.

BRIEF SUMMARY OF THE INVENTION

'NJ360' differs from the related cultivar 'White Lady' (U.S. Plant Pat. No. 5,821), in that trees of 'NJ360' crop more consistently are less susceptible bacterial leaf spot (*Xanthomonas campestris* pv. *pruni*) than 'White Lady'. The 'NJ360' variety is also distinguished from other peach varieties due to the following unique combination of characteristics:

Produces medium to large, nearly round, semi-freestone fruit with a low tendency to split when adequately cropped.

Fruits have an attractive red to greyed-purple blush over a bright yellow-white ground color.

Excellent production of fruit that ripen in mid-season on trees with low susceptibility to bacterial leaf spot.

Fruit have superior eating quality due to their aromatic, sweet, and sub-acid flavor.

The variety was asexually reproduced at a fruit research farm in Cream Ridge, N.J. Asexual reproduction of this new variety by budding onto >Lovell=peach seedling rootstock (non-patented) shows that the foregoing characteristics are so reproduced.

The following detailed description concerns the original tree, 'NJ360'. The original tree and asexual progeny have been observed growing in a cultivated area at a fruit research farm in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions unless the context clearly indicates otherwise. Color designations are made with reference to *The Royal Horticultural Society* (*R.H.S.*) *Colour Chart* (1966 Ed.)

BRIEF DESCRIPTION OF THE DRAWINGS

This new variety is illustrated by the accompanying photographic drawings of the 'NJ360' plant at approximately seven (7) years old, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
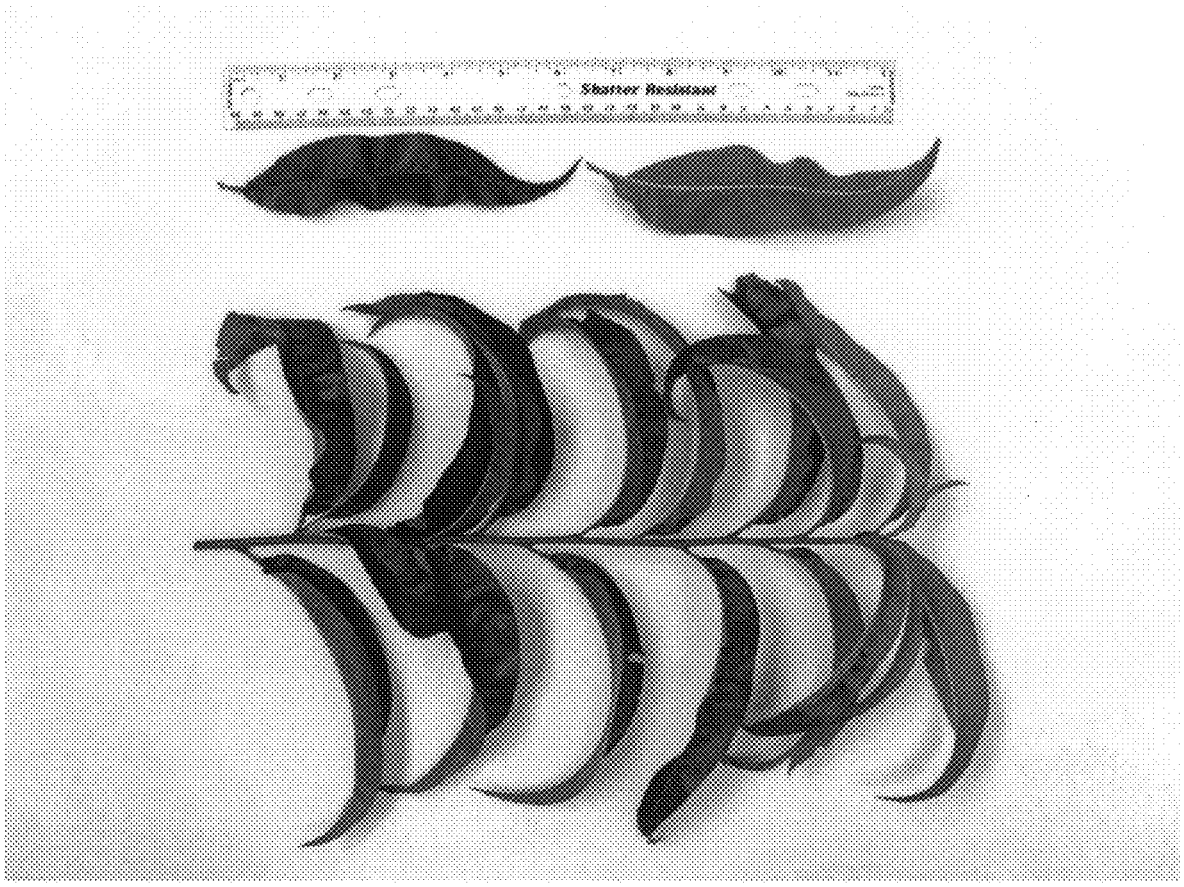
FIG. 1 is a color photograph taken on Aug. 12, 2019 of a characteristic twig of 'NJ360' in mid-summer bearing typical leaves of the foliage.
Figure 2:
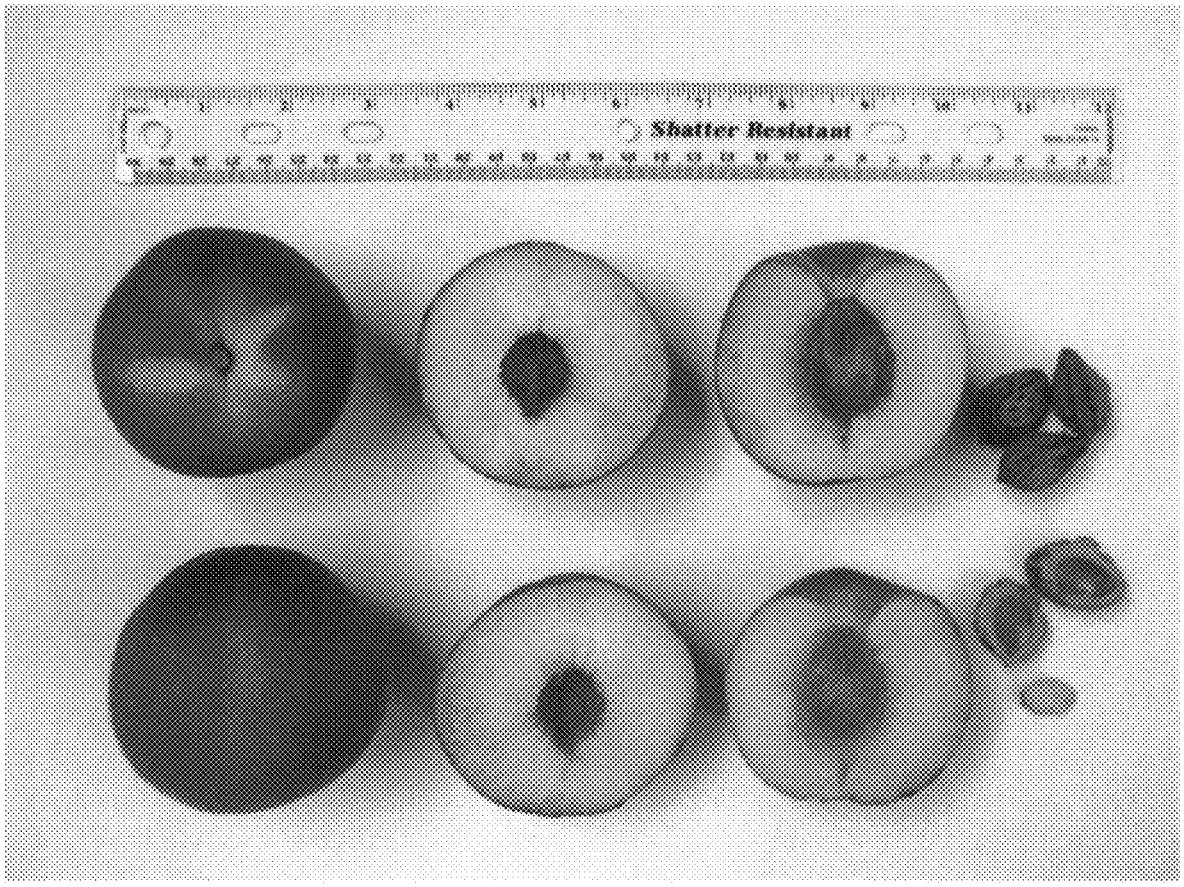
FIG. 2 is a color photograph taken on Jul. 29, 2019 of characteristic mature fruit and stones of 'NJ360'. Whole fruit are presented in two positions and both a transverse and longitudinal cross section to illustrate that the pericarp partially adheres to the pit when the fruit is mature. The stones exemplify the obovate shape and pits and grooves on the surface of the stone.
Figure 3:
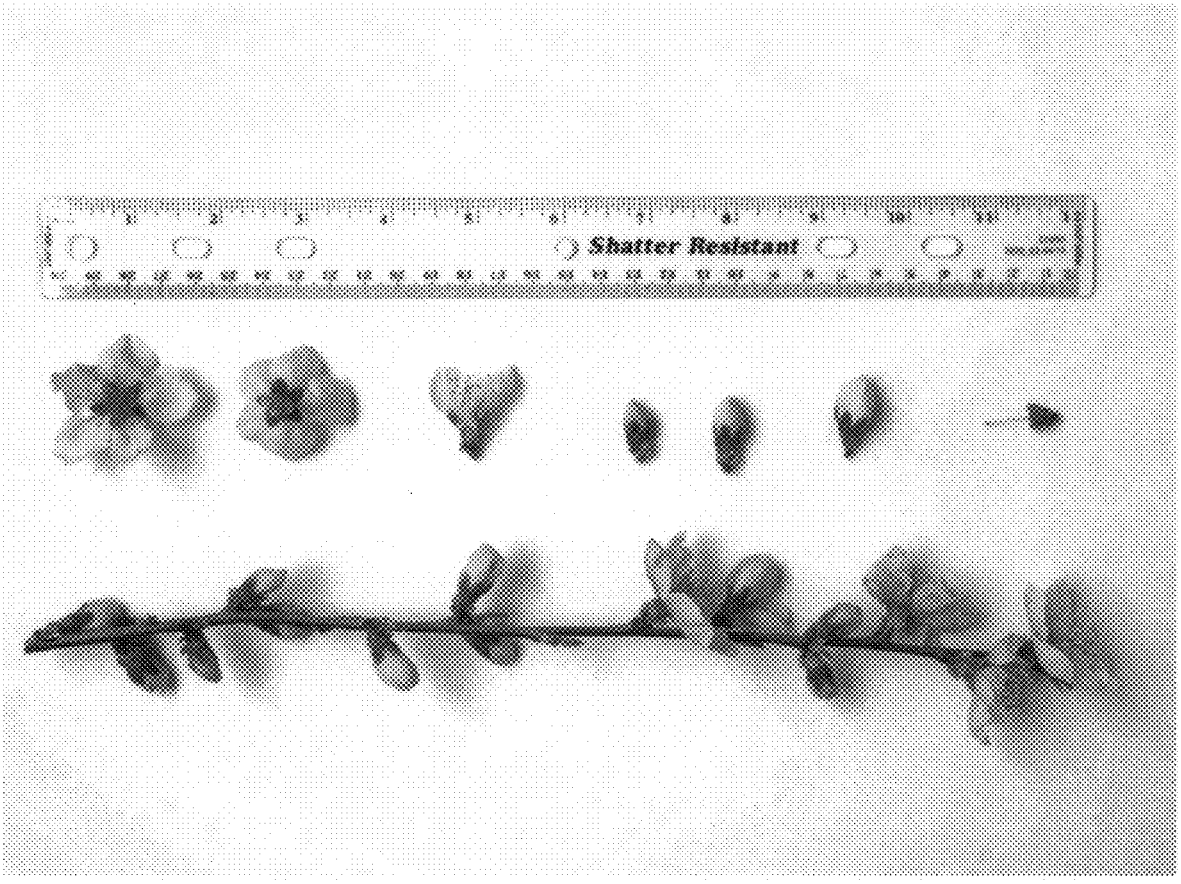
FIG. 3 is a color photograph of a characteristic twig that illustrates the typical flower buds and large, showy flowers of 'NJ360' observed on a tree at a fruit research farm in Cream Ridge, N.J. on Apr. 9, 2019.
Figure 4:
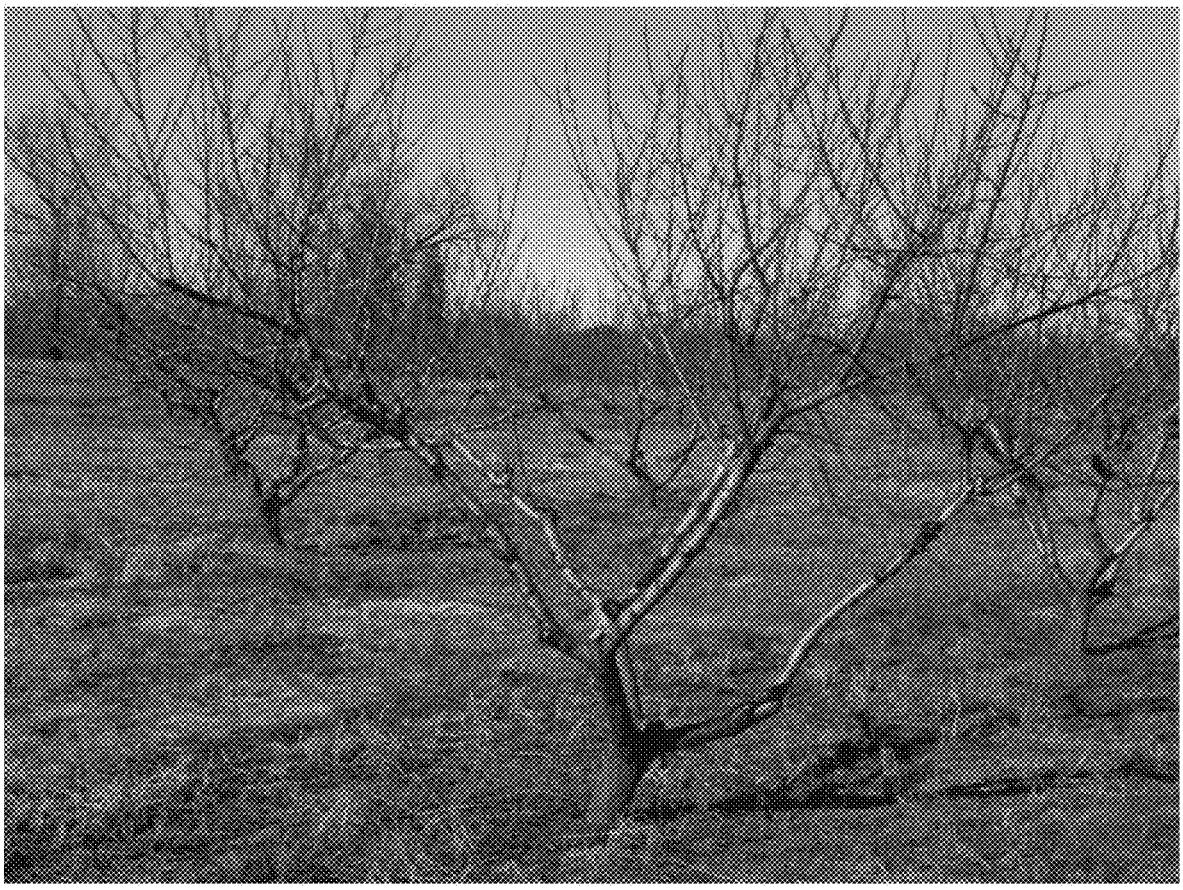
FIG. 4 is a color photograph of a dormant tree of 'NJ360', prior to pruning, in early spring that illustrates the spreading growth habit of a tree at the fruit research farm in Cream Ridge, N.J. on Mar. 26, 2019.
Figure 5:
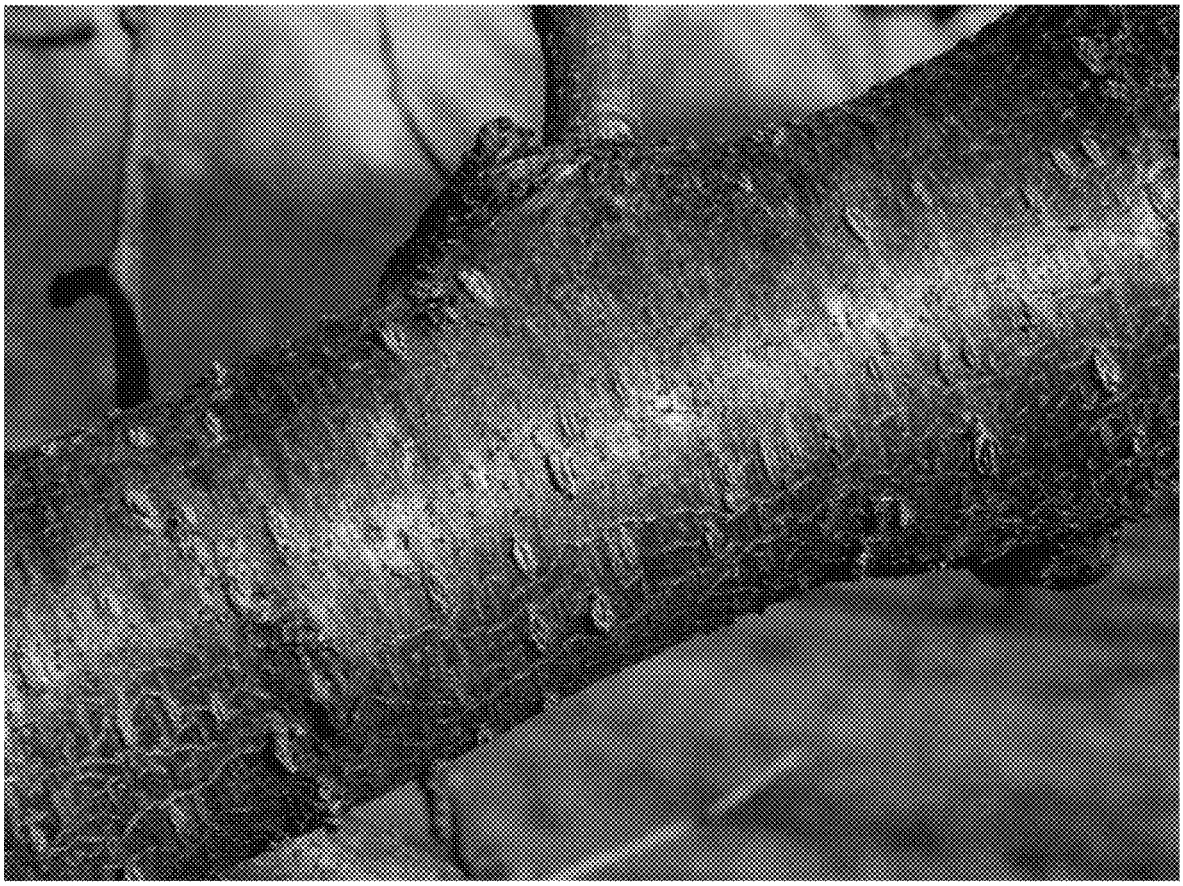
FIG. 5 is a color photograph taken on Sep. 26, 2019 of immature bark of 'NJ360' that illustrates color and the moderate density of conspicuous elliptic lenticels on the immature bark.
Figure 6:
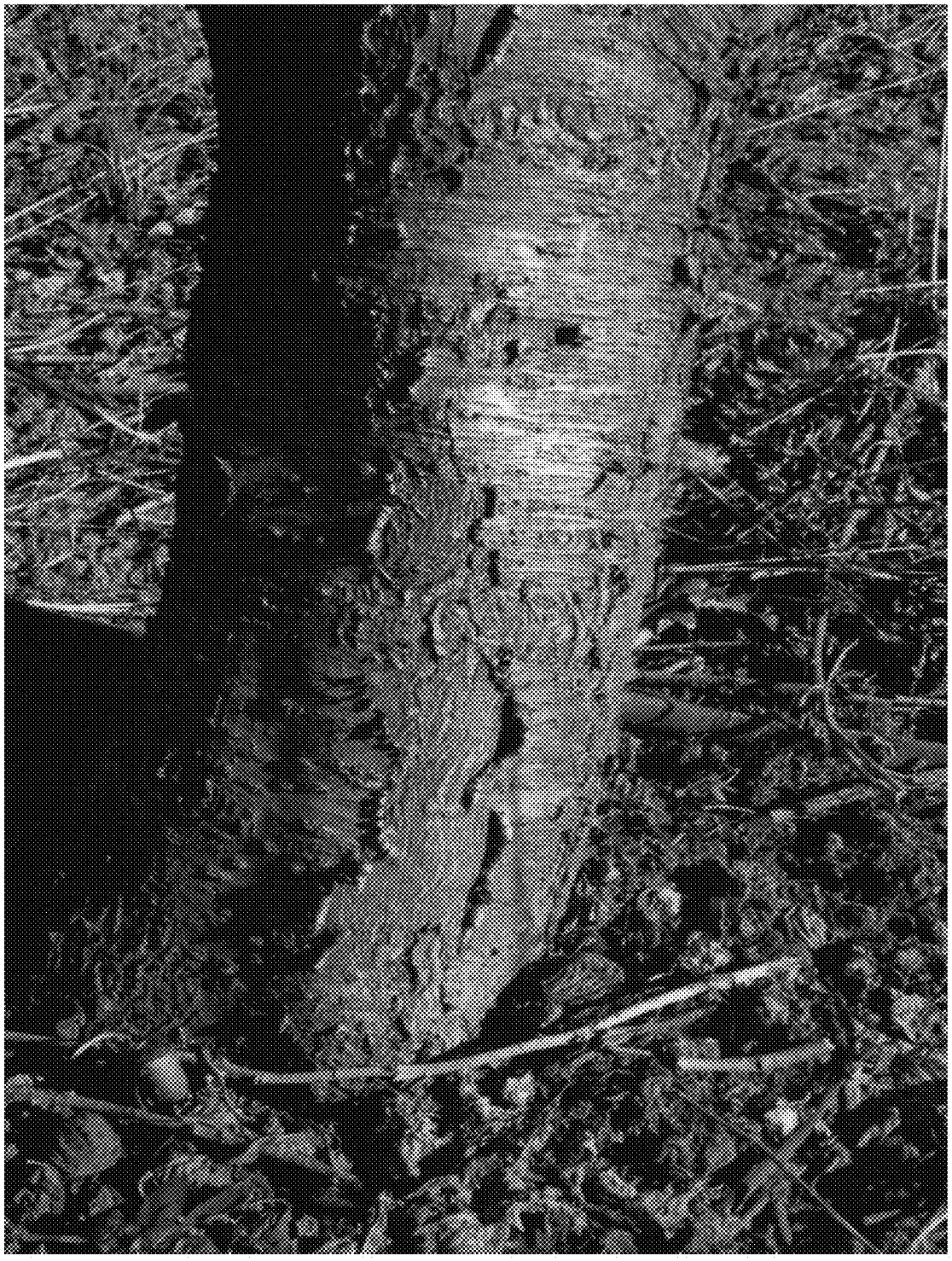
FIG. 6 is a color photograph taken on Sep. 26, 2019 of mature bark of 'NJ360' that illustrates the greyed-green color, slightly rough texture, with sparse, broad, very shallow furrows on the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJ360' variety is based on observations of an asexually reproduced tree. The observed tree was seven years of age and growing on 'Lovell' seedling rootstock (non-patented) at the fruit research farm in Cream Ridge, N.J.

Scientific name: *Prunus persica* L.

Parentage:

*Seed parent*.—'H24-128-01224'.

*Pollen parent*.—'NJ354'.

Tree:

*Vigor*.—Vigorous.

*Plant hardiness zone*.—Growth of plants has only been observed in zone 6b.

*Dormant flower bud cold tolerance*.—At least to −21° C.

*Leaf bud burst*.—Typically in mid-April when grown in Cream Ridge, N.J., but can vary by one to two weeks.

*Overall shape*.—Spreading.

*Height*.—Average as compared to other peach cultivars. For example, measurement of a typical grafted tree on 'Lovell' peach seedling rootstock (non-patented) at seven years after planting shows an average height of 3.4 meters when grown in Cream Ridge, N.J.

*Width*.—Average as compared to other peach cultivars. For example, measurement of a typical grafted tree on 'Lovell' peach seedling rootstock (non-patented) at seven years after planting shows an average width of 4.6 meters when grown in Cream Ridge, N.J.

*Caliper*.—Seven-year-old tree is 58 cm. in circumference measured at 20 cm. from the ground.

Trunk and branches:

*Trunk bark texture*.—Slightly rough, with sparse, broad, very shallow furrows.

*Trunk bark color*.—Greyed-green (RHS 198A).

*Primary branches*.—Branches that are approximately 15 cm. in circumference are greyed-green (between RHS 198C and RHS 198D).

*Lenticels*.—Moderate density, approximately 0.7 per square cm; elliptical in shape and conspicuous; typical examples of which averaged 4.6 mm. in length and 1.8 mm. in width; greyed-green (RHS 198D) in color becoming greyed-orange (RHS 173C) towards the center.

*Branch pubescence*.—None.

*New growth bark*.—Greyed-purple (between RHS 184A and RHS 184B) in sun; yellow-green (between RHS 145D and RHS 145B) in shade.

*Internodes*.—Length averaging 20.8 mm. on a one-year shoot.

Leaves:

*Texture*.—Glabrous, both surfaces.

*Sheen*.—Young leaves satin to semi-glossy with a flat finish on the underside.

*Length*.—About 165 mm to 185 mm., averaging about 173 mm. including the petiole.

*Width*.—About 35 mm. to 45 mm., averaging about 40 mm.

*Petiole*.—Averaging 11.6 mm. long and about 1.9 mm. in diameter; Color: Yellow-green (RHS 146B).

*Margin*.—Crenate.

*Margin undulation*.—Moderate.

*Form*.—Lanceolate, and concave in cross section.

*Apex*.—Sharply acute, curved downward.

*Base*.—Acute.

*Venation*.—Pinnate.

*Glands*.—

*Number*.—About 2 to 4, averaging about 3.3.

*Position*.—Mostly located on the petiole.

*Size*.—Length averaging 2.1 mm. and width averaging 1.1 mm.

*Form*.—Reniform.

*Stipules*.—Stipules are present on immature leaves, but they are not persistent. Typically, there are two per immature leaf, with an average length of 8.4 mm. The color is yellow-green (RHS 152A), becoming greyed-purple (between RHS 183A and RHS 183B) just prior to dehiscence. None observed on mature leaves.

*Leaf color*.—

*Upper leaf surface*.—Green (between RHS 137B and RHS 137C).

*Lower leaf surface*.—Yellow-green (RHS 147B).

*Vein*.—Yellow-green (between RHS 145C and RHS 145D).

*Pubescence*.—None.

Flowers:

*Size*.—Large size, typical flower measuring between 34 mm. and 42 mm, averaging about 38 mm across.

*Color.*—

*Dormant bud.*—Grey (RHS 201D) becoming grey (RHS 201A) near the base.

*Pink stage bud.*—Red-purple (between RHS 62A and RHS 62B).

*Open flower.*—Red-purple (RHS 62D).

*Petals.*—Typically five petals per flower; slightly cupped, nearly round, with slight undulation on some petals, averaging about 20 mm. long and 16 mm. wide.

*Petal apex.*—Obtuse, nearly rounded.

*Petal base.*—Cuneate.

*Stamens.*—

*Number.*—Variable, typical range 38 and 41, averaging 40.

*Position.*—Perigynous and near the point of attachment of the petals.

*Length.*—Variable, between 10.4 mm. to 13.8 mm, averaging 12.6 mm.

*Filament color.*—Red-purple (RHS 69A).

*Anther color.*—Adaxial and abaxial surface is greyed-purple (RHS 184A).

*Stigma.*—Located approximately at the same level as the majority of the stamens.

*Pistil.*—

*Number.*—One.

*Size.*—Length between 17 and 22 mm, averaging 20 mm.

*Pistil color.*—Yellow-green (RHS 151A).

*Ovary.*—Moderate, dense pubescence about 0.5mm. in length and ellipsoid in shape, color yellow-green (RHS 145D).

*Sepals.*—

*Number.*—Five.

*Pubescence.*—Length short, fine, low density becoming moderate at the margin.

*Color.*—Greyed-purple (RHS 183A).

*Shape.*—Triangular, with a rounded apex.

*Size.*—Length averaging 5.0 mm., width averaging 4.4 mm

*Nectar cup color.*—Greyed-yellow (RHS 162A).

*Pollen.*—Abundant, viable and plant is typically self-fruitful; Color is greyed-yellow (RHS 162A).

*Fragrance.*—Nearly none.

*Bloom season.*—Onset of bloom at Cream Ridge, N.J. in 2019 on April 8; full bloom on April 13.

Fruit:

*Size.*—Medium to large, averaging about 6.3 cm. long, 6.8 cm. wide parallel to the suture and 7.80 cm. wide perpendicular to the suture.

*Typical weight.*—Between 150 to 200 g, averaging about 170 g.

*Form.*—

*Longitudinal section.*—Nearly round.

*Traverse section.*—Nearly round.

*Suture.*—Shallow.

*Ventral surface.*—Nearly smooth.

*Base.*—Round.

*Apex.*—Flat; apex tip is a small point.

*Stem.*—Average length of 9.7 mm. and an average diameter of 3.8 mm.

*Skin.*—

*Thickness.*—Medium.

*Surface.*—Pubescent, moderate density, typically less than 1mm in length.

*Tenacity.*—Medium.

*Astringency.*—None.

*Tendency to crack.*—Low.

*Color.*—Blush is red (RHS 46A) in partial sun; greyed-purple (RHS 183A) in full sun; ground color is yellow-white (RHS 158A).

*Fruit properties.*—

*Flesh color.*—Yellow-white (between RHS 158B and RHS 158C), mottled with red (RHS 42A) in the flesh and adjacent to stone.

*Flesh firmness.*—Above average.

*Flesh adhesion.*—Semi-freestone.

*Juice.*—Moderate.

*Texture.*—Firm but melting.

*Fibers.*—Not noticeable.

*Ripens.*—Between July 27 and August 8 at Cream Ridge, N.J.

*Flavor.*—Sweet, subacid.

*Soluble solids.*—13.8%.

*Aroma.*—Slight to moderate.

*Eating quality.*—Very good.

*Keeping quality.*—Medium. Has held its flavor and firmness for at least 14 days in cold storage at 1° C. to 2° C.

*Shipping quality.*—Good. No bruising or scaring disorders have been observed.

*Usage.*—Dessert.

*Market.*—Local and long distance.

*Productivity.*—Excellent, though varies greatly depending upon conditions inclusive of winter and spring temperatures, rainfall, tree density, pruning methods, soil type, fertilization, irrigation, and degree of fruit thinning Trees have produced a full crop in 9 out of 10 years in Cream Ridge, N.J.

Stone:

*Type.*—Semi-freestone.

*Form.*—Obovate.

*Base.*—Medium.

*Apex.*—Medium.

*Surface.*—Pits and grooves.

*Ventral suture.*—Medium.

*Dorsal ridge.*—Medium height, narrow width, forming deep lines.

*External color.*—Greyed-orange (between RHS 174C and RHS 174D).

*Cavity surface color.*—Greyed-orange (between RHS 165C and RHS 165D).

*Average stone dry weight.*—4.0 g.

*Average stone wall thickness.*—Varies between 4.1 mm. along the dorsal ridge to 9.2 mm. at the base.

*Size.*—Averages about 29.1 mm. long, 21.8 mm wide parallel to the dorsal ridge, and 17.2 mm wide perpendicular to the dorsal ridge.

*Tendency to split.*—Typically low.

Kernel:

*Dry weight.*—0.2 g.

*Form.*—Elliptic.

*Skin color.*—Greyed-orange (RHS 164B).

*Vein color.*—Greyed-orange (RHS 164A).

*Viability.*—Marginal.

*Size.*—Averages about 15.7 mm. long, 9.3 mm wide, and 2.5 mm. in breadth.

*Plant/fruit disease and pest resistance/susceptibility.*—No atypical resistances/susceptibilities have been noted under normal cultural practices.

We claim:

1. A new and distinct variety of peach tree, substantially as herein shown and described.

* * * * *